(12) United States Patent
Della Ciana et al.

(10) Patent No.: US 11,761,964 B2
(45) Date of Patent: Sep. 19, 2023

(54) ULTRA-SENSITIVE CHEMILUMINESCENT SUBSTRATES FOR PEROXIDASE

(71) Applicant: CYANAGEN S.r.l., Bologna (IT)

(72) Inventors: Leopoldo Della Ciana, Bologna (IT); Lorenzo Biagini, Bologna (IT); Thomas Paul Jansen, Bologna (IT); Rossana Perciaccante, Bologna (IT); Manuela Vargiolu, Bologna (IT); Marina Eleonora Vettraino, Bologna (IT)

(73) Assignee: CYANAGEN S.r.l., Bologna (IT)

(*) Notice: Subject to any disclaimer, the term of this patent is extended or adjusted under 35 U.S.C. 154(b) by 528 days.

(21) Appl. No.: 16/749,162

(22) Filed: Jan. 22, 2020

(65) Prior Publication Data

US 2020/0232991 A1 Jul. 23, 2020

(30) Foreign Application Priority Data

Jan. 22, 2019 (IT) .................. 102019000000959

(51) Int. Cl.
  *G01N 33/58* (2006.01)
  *C09K 11/07* (2006.01)
  *G01N 33/535* (2006.01)

(52) U.S. Cl.
  CPC ............ *G01N 33/581* (2013.01); *C09K 11/07* (2013.01); *G01N 33/582* (2013.01); *C09K 2211/1037* (2013.01); *G01N 33/535* (2013.01)

(58) Field of Classification Search
  CPC .................. C07D 471/04; C09K 11/07; C09K 2211/1029; C09K 2211/1037;
  (Continued)

(56) References Cited

U.S. PATENT DOCUMENTS

2021/0231572 A1* 7/2021 Della Ciana ............. C12Q 1/28

FOREIGN PATENT DOCUMENTS

EP  0 491 477  6/1992
EP  1 962 095  8/2008
(Continued)

OTHER PUBLICATIONS

Nishinaka et al. A new sensitive chemiluminescence probe, L-012, for measuring the production of superoxide anion by cells. Biochemical and Biophysical Research Communications 1993, vol. 193, No. 2, pp. 554-559. (Year: 1993).*

(Continued)

*Primary Examiner* — Shafiqul Haq
(74) *Attorney, Agent, or Firm* — Nixon & Vanderhye P.C.

(57) ABSTRACT

A method for increasing the light emission produced by the chemiluminescent reaction of 8-amino-5-chloro-7-phenylpyrido[3,4-d]pyridazine-1,4(2H,3H)-dione, a peroxidase enzyme or a conjugate thereof, an enhancer, a co-enhancer and a peroxide oxidizer, wherein the enhancer is an anionic N-alkylphenothiazine and the co-enhancer is selected from a 4-dialkylaminopyridine or an N-azole, and
wherein the method comprises the following steps:
  i. realizing a chemiluminescent substrate by means of mixing together 8-amino-5-chloro-7-phenylpyrido[3,4-d]pyridazine-1,4(2H,3H)-dione, the enhancer, the co-enhancer and the peroxide oxidizer, and
  ii. adding the peroxidase enzyme or a conjugate thereof to the chemiluminescent substrate.

8 Claims, 13 Drawing Sheets

(58) Field of Classification Search
CPC .. C09K 2211/1059; C12Q 1/28; G01N 21/76; G01N 33/5306; G01N 33/581; G01N 33/582; G01N 33/535
See application file for complete search history.

(56) References Cited

FOREIGN PATENT DOCUMENTS

| | | |
|---|---|---|
| EP | 2 405 016 | 1/2012 |
| WO | 94/23060 | 10/1994 |

OTHER PUBLICATIONS

Zielonka et al. On the use of L-012, a luminol-based chemiluminescent probe, for detecting superoxide and identifying inhibitors of NADPH oxidase: a reevaluation. Free Radical Biology and Medicine 2013, vol. 65, pp. 1310-1314. (Year: 2013).*

Search Report for IT102019000000959, dated Sep. 18, 2019, 8 pages.

Chen et al., "A Review of Enhancers for Chemiluminescence Enzyme Immunoassay", Food and Agricultural Immunology, vol. 28, No. 2, Mar. 4, 2017, pp. 315-327.

Ichibangase et al., "Evaluation of lophine derivatives as L-012 (luminol analog)-dependent chemiluminescence enhancers for measuring horseradish peroxidase and $H_2O_2$ : Evaluation of lophine derivatives as L-012-dependent CL enhancer", Luminescence: The Journal of Biological and Chemical Luminescence vol. 29, No. 2, Mar. 1, 2014, pp. 118-121.

* cited by examiner

SPTZ

SBTZ

CPTZ

CBTZ

L-012/B3

Westar Supernova

ULTRA-SENSITIVE CHEMILUMINESCENT SUBSTRATES FOR PEROXIDASE

This application claims priority to IT Patent Application No. 102019000000959 filed 22 Jan. 2019, the entire contents of which is hereby incorporated by reference.

FIELD OF THE INVENTION

The present invention concerns a chemiluminescent substrate for assaying peroxidases in an assay for determining an analyte in a sample, wherein the chemiluminescent substrate allows quantitative peroxidase detection with a very high sensitivity.

BACKGROUND ART

The chemiluminescent oxidation of luminol catalyzed by horseradish peroxidase (HRP) finds wide employment in analytical tests of antigens, antibodies and nucleic acids, and, in particular, blotting tests, e.g. Dot Blots, Western Blots (proteins), Southern and Northern Blots (nucleic acids).

It is known that the chemiluminescent oxidation of luminol catalyzed by HRP can be made faster and more efficient by adding an electron mediator, or enhancer, as shown, for example, by Kricka L J (1991), *Clinical Chemistry*, 37:1472-1481; or by Kricka L J, Voyta J C and Bronstein I in "Chemiluminescent Methods for Detecting and Quantitating Enzyme Activity" (2000), *Methods Enzymol;* 305:370-390.

The mechanism of the enhanced chemiluminescence reaction (ECL), where luminol and an enhancer are oxidized simultaneously, has been described as follows [Lind J, Merenyi G, and Eriksen T E (1983), *J Am Chem Soc,* 105: 7655-7661]. In the first step of ECL, the enhancer (E), which is a more active substrate for HRP than luminol, is oxidized by hydrogen peroxide in the presence of HRP according to a "ping-pong" mechanism:

$$HRP+H_2O_2 \rightarrow HRP\text{-}I \qquad (1)$$

$$HRP\text{-}I+E \rightarrow HRP\text{-}II+E. \qquad (2)$$

$$HRP\text{-}II+E \rightarrow HRP+E. \qquad (3)$$

where E is the enhancer, E. is a radical product of one-electron oxidation of the enhancer, HRP is the Horseradish Peroxidase enzyme in its Fe(III) resting state, HRP-I and HRP-II are the oxidized intermediates of the peroxidase, which are, by two and one oxidation equivalents, above the resting state, respectively. Then, the radical product of the enhancer (E.) reacts reversibly with a luminol molecule (LH$^-$) [Easton P M, Simmonds A C, Rakishev A, Egorov A M, and Candelas L P (1996), *J Am Chem Soc;* 118:6619-6624]:

$$E.+LH^- \leftrightarrows E+L.^- \qquad (4)$$

Thermodynamically, the position of redox equilibrium (4) is determined by the difference between the reduction potentials of the enhancer and luminol radicals under the conditions of the experiment. Once formed, two luminol radicals (L.$^-$) dismute to luminol anion (LH$^-$) and diazaquinone intermediate (L):

$$2L.^- \rightarrow LH^- + L \qquad (5)$$

The diazaquinone intermediate (L) reacts with hydrogen peroxide with formation of a luminol peroxide (LO$_2^{2-}$), which collapses to the excited state of 3-aminophthalate ([AP$^{2-}$]*) with expulsion of molecular nitrogen; [AP$^{2-}$]* then returns to the ground state (AP$^{2-}$) with emission of a photon (hv) at 425 nm:

$$L+H_2O_2 \rightarrow LO_2^{2-} \rightarrow [AP^{2-}]^* + N_2 \rightarrow AP^{2-} + h\nu \qquad (6)$$

The intensity of emitted light is proportional to the square of the rate of generation of luminol radicals (L.$^-$). The quadratic relation is a consequence of the mechanism of generation of the excited species, which involves the dismutation of two luminol radicals, Equation 5. In turn, the rate of generation of luminol radicals is given by the rate of enzyme turnover, weighted by the fraction of the radicals generated that result in luminol radicals (L.$^-$) after redox equilibrium (4). The rate of enzyme turnover is governed by the rate-determining step, the reduction of HRP-II to ferric enzyme (HRP), Equation (3). In conclusion, the enhancement of chemiluminescence can be described to a good approximation by considering (a) the acceleration of the enzyme turnover by reaction of the enhancer with HRP-II and (b) the reversible electron-transfer reaction between the enhancer radical and luminol.

A number of compounds were successfully used in the enhancement of HRP-induced chemiluminescence including: luciferin, 6-hydroxybenzotriazols, p-iodophenols, p-coumaric acid and other phenolic enhancers (Thorpe G H G and Kricka L J (1986), *Methods Enzymol;* 133:331); aromatic amines (U.S. Pat. No. 4,279,950); acetanilides (Eur. Pat. Appl. No. 603953); N-substituted phenothiazines (U.S. Pat. Nos. 5,171,688 and 6,432,662); boronic acids (U.S. Pat. No. 5,629,168).

One fundamental limitation in terms of chemiluminescent light output of luminol based substrates relates to its relative low luminescent quantum yield, Eq. (6). For this reason a number of luminol analogs have been developed, most notably 8-amino-5-chloro-7-phenylpyrido[3,4-d]pyridazine-1,4(2H,3H)-dione, also known as L-012 (Eur. Pat. Appl. No. 491477), having the following chemical structure:

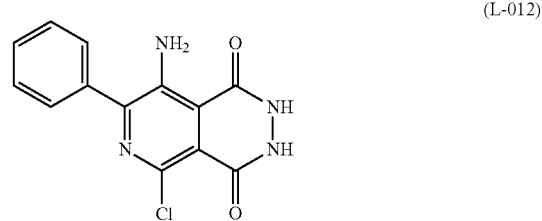 [SMILES: Nc1c(-c2ccccc2)nc(Cl)c2c(=O)[nH][nH]c(=O)c12]

(L-012)

Thus, in p-iodophenol and boronate enhanced chemiluminescent assays for horseradish peroxidase, this compound exhibited increases in light emission of up to 10-fold in comparison with luminol [Ji X, Kondo K, Aramaki Y, and Kricka L J (1996) *J Biolumin Chemilumin;* 11:1-7].

More recently, several compounds belonging to the class of lophines were tested as enhancers in 8-amino-5-chloro-7-phenylpyrido[3,4-d]pyridazine-1,4(2H,3H)-dione substrates. In particular, with 2-(4-hydroxyphenyl)-4,5-di(2-pyridyl)imidazole as enhancer the chemiluminescence system sensitivity was found to be 20-times higher than that of the conventional enhanced luminol system using 4-iodophenol [Ichibangase T, Ohba Y, Kishikawa N, Nakashima K, and Kuroda N (2014) *Luminescence* 29:118-121].

However, recent developments in luminol based technology have led to chemiluminescent HRP substrates at least as sensitive as those based on L-012 [U.S. Pat. No. 7,803,573 (2010), U.S. Pat. No. 9,040,252 (2015)]

Thus, given the higher chemiluminescent efficiency of the chemiluminescent compound L-012 compared to luminol, there is still ample potential for further increasing the sensitivity of peroxidase enzyme detection.

OBJECT AND SUMMARY OF THE INVENTION

Object of the present invention is to provide an ultra-sensitive chemiluminescent substrate for quantitatively determining a peroxidase enzyme in assays for the detection of an analyte in a sample.

According to the invention, the above object is achieved thanks to the kits specified in the ensuing claims, which are understood as forming an integral part of the present description.

According to one embodiment, the present disclosure concerns a method for increasing the light emission produced by the chemiluminescent reaction of 8-amino-5-chloro-7-phenylpyrido[3,4-d]pyridazine-1,4(2H,3H)-dione, a peroxidase enzyme, an enhancer, a co-enhancer and a peroxide oxidizer, wherein the enhancer is an anionic N-alkylphenothiazine and the co-enhancer is selected from a 4-dialkylaminopyridine or an N-azole.

The present invention also concerns a kit for performing the method for increasing the light emission produced by the chemiluminescent reaction of 8-amino-5-chloro-7-phenylpyrido[3,4-d]pyridazine-1,4(2H,3H)-dione as disclosed herein, wherein the kit comprises 8-amino-5-chloro-7-phenylpyrido[3,4-d]pyridazine-1,4(2H,3H)-dione, a peroxide oxidizer, an enhancer and a co-enhancer, wherein the enhancer is an anionic N-alkylphenothiazine and the co-enhancer is selected from a 4-dialkylaminopyridine or an N-azole.

BRIEF DESCRIPTION OF THE DRAWINGS

The invention will now be described, by way of example only, with reference to the enclosed figures of drawing, wherein.

DETAILED DESCRIPTION OF THE INVENTION

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

The present disclosure discloses a method for performing a chemiluminescent assay for detecting an analyte in a sample comprising:

a. reacting the analyte with an analyte detecting reagent, wherein the detecting reagent is directly or indirectly conjugated with a peroxidase enzyme, with formation of a complex analyte-detecting reagent;

b. reacting the complex analyte-detecting reagent with a chemiluminescent substrate comprising an enhancer, a co-enhancer, a peroxide oxidizer and 8-amino-5-chloro-7-phenylpyrido[3,4-d]pyridazine-1,4(2H,3H)-dione, that co-react in a chemiluminescent reaction with light emission, wherein the enhancer is an anionic N-alkylphenothiazine and the co-enhancer is selected between a 4-dialkylaminopyridine and an N-azole; and c. detecting the analyte by means of measurement of the light emission.

In an embodiment, the present invention concerns a method for increasing the light emission produced by the chemiluminescent reaction of 8-amino-5-chloro-7-phenylpyrido[3,4-d]pyridazine-1,4(2H,3H)-dione, a peroxidase enzyme or a conjugate thereof, an enhancer, a co-enhancer and a peroxide oxidizer, wherein the enhancer is an anionic N-alkylphenothiazine and the co-enhancer is selected from a 4-dialkylaminopyridine or an N-azole, wherein the method comprises the following steps:

(i) realizing a chemiluminescent substrate by means of mixing together 8-amino-5-chloro-7-phenylpyrido[3,4-d]pyridazine-1,4(2H,3H)-dione, the enhancer, the co-enhancer and the peroxide oxidizer, and (ii) adding the peroxidase enzyme or a conjugate thereof to the chemiluminescent substrate.

Figure 1:
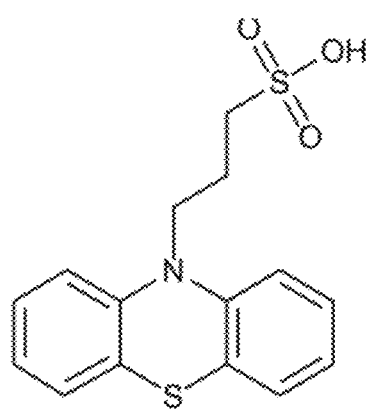
FIG. 1 shows the structures of anionic N-alkylphenothiazine enhancers of this invention.
Figure 1:
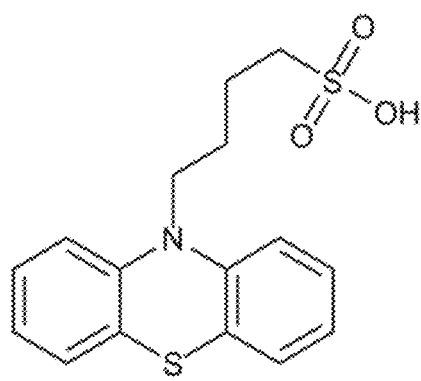
Figure 1:
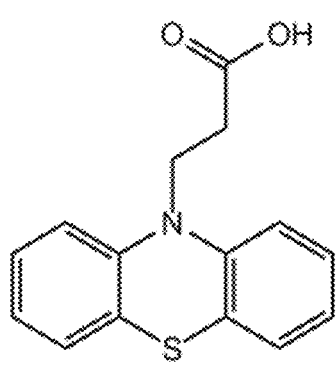
Figure 1:
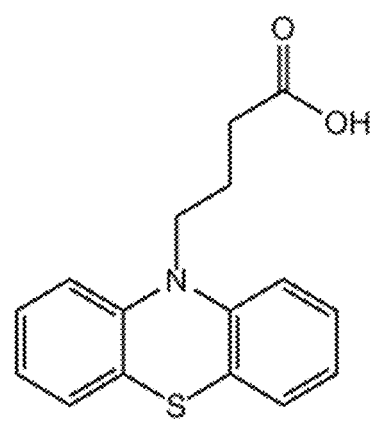

In an embodiment, the anionic N-alkylphenothiazine is selected from the group consisting of 3-(10H-phenothiazin-10-yl)propane-1-sulfonic acid (SPTZ), 4-(10H-phenothiazin-10-yl)butane-1-sulfonic acid (SBTZ), 3-(10H-phenothiazine-10-yl)propanoic acid (CPTZ) and 4-(10H-phenothiazine-10-yl)butanoic acid (CBTZ) and their salts. The chemical structures of these N-alkylphenothiazines are shown in FIG. 1.

A co-enhancer, or secondary enhancer, is defined as a compound, which by itself has no enhancing effect on the chemiluminescent reaction of luminol or its analogs, while it increases the light output when used in conjunction with an enhancer, see Marzocchi E, Grilli S, Della Ciana L, Prodi L, Mirasoli M, and Roda A (2008) *Anal biochem,* 377:189-194; Vdovenko M M, Della Ciana L, and Sakharov I Y (2009) *Anal Biochem,* 392:54-58. The increase in light output has been attributed to a corresponding increase in the peroxidase enzyme turnover, see Sakharov I Y, and Vdovenko M M (2013) *Anal Biochem,* 434:12-14.

Co-enhancers of the present invention belong to two different classes of compounds, 4-dialkylaminopyridines (as described in U.S. Pat. No. 7,803,573), and N-azoles (as described in U.S. Pat. No. 9,040,252). Among 4-dialkylaminopyridines, preferred compounds are 4-morpholino-pyridine (MORP), 4-dimethylaminopyridine (DMAP) and 4-pyrrolidinopyridine (PPY). Among N-azoles, preferred compounds are imidazole and 1-methylimidazole.

The peroxide oxidizer can be hydrogen peroxide, or any complex of hydrogen peroxide, which—upon dissolution in aqueous solution—releases hydrogen peroxide, such as perborates, percarbonates or the urea/hydrogen peroxide complex in a molar ratio equal to 1:1. In a preferred embodiment, the peroxide oxidizer is selected among hydrogen peroxide, urea/hydrogen peroxide complex, a perborate salt, a percarbonate salt.

The peroxidase enzyme is any peroxidase suitable for use in chemiluminescence assays. According to an embodiment, the peroxidase enzyme is selected among horseradish peroxidase (for example Sigma type VIA or IX), or an anionic peroxidase, like soybean peroxidase and sweet potato peroxidase. The peroxidase enzyme can be either conjugated or not conjugated with a detecting reagent for the analyte to be detected.

According to an embodiment, the concentration of the chemiluminescent compound, 8-amino-5-chloro-7-phenylpyrido[3,4-d]pyridazine-1,4(2H,3H)-dione, in the chemiluminescent substrate is comprised between 0.01 mM and 1 mM, preferably between 0.05 and 0.5 mM.

According to an embodiment, the concentration of the anionic N-alkylphenothiazine enhancer in the chemiluminescent substrate is comprised between 0.1 and 10 mM, preferably between 0.5 and 5 mM.

According to an embodiment, the concentration of the co-enhancer in the chemiluminescent substrate is comprised between 0.1 and 100 mM, preferably between 0.5 and 50 mM.

According to an embodiment, the concentration of the peroxide in the chemiluminescent substrate is comprised between 0.1 and 10 mM, preferably between 0.5 and 8 mM.

According to an embodiment, the pH of the chemiluminescent substrate is comprised between 5.0 and 9.0, preferably between 6.0 and 8.5.

According to a preferred embodiment, the chemiluminescent substrate, having a pH comprised between 5.0 and 9.0, preferably between 6.0 and 8.5, contains:
i) 8-amino-5-chloro-7-phenylpyrido[3,4-d]pyridazine-1,4(2H,3H)-dione in a concentration between 0.01 mM and 1 mM, preferably between 0.05 and 0.5 mM;
ii) the anionic N-alkylphenothiazine enhancer in a concentration between 0.1 and 10 mM, preferably between 0.5 and 5 mM;
iii) the co-enhancer in a concentration between 0.1 and 100 mM, preferably between 0.5 and 50 mM;
iv) the peroxide oxidizer in a concentration between 0.1 and 10 mM, preferably between 0.5 and 8 mM.

According to one embodiment, the method further comprises a step of detecting an analyte in a sample through measuring the light emission produced by the chemiluminescent reaction of 8-amino-5-chloro-7-phenylpyrido[3,4-d]pyridazine-1,4(2H,3H)-dione, a peroxidase enzyme, a peroxide oxidizer, an enhancer and a co-enhancer.

The present invention also concerns a kit for performing the method for increasing the light emission produced by the chemiluminescent reaction of 8-amino-5-chloro-7-phenylpyrido[3,4-d]pyridazine-1,4(2H,3H)-dione as disclosed herein, wherein the kit comprises 8-amino-5-chloro-7-phenylpyrido[3,4-d]pyridazine-1,4(2H,3H)-dione, a peroxide oxidizer, an enhancer and a co-enhancer, wherein the enhancer is an anionic N-alkylphenothiazine and the co-enhancer is selected from a 4-dialkylaminopyridine or an N-azole.

In an embodiment, the anionic N-alkylphenothiazine is selected from the group consisting of 3-(10H-phenothiazin-10-yl)propane-1-sulfonic acid, 4-(10H-phenothiazin-10-yl)butane-1-sulfonic acid, 3-(10H-phenothiazin-10-yl)propanoic acid and 4-(10H-phenothiazine-10-yl)butanoic acid, and their salts.

In an embodiment, the co-enhancer is selected among imidazole, 1-methylimidazole, 4-morpholinopyridine (MORP), 4-dimethylaminopyridine (DMAP) and 4-pyrrolidinopyridine (PPY).

In an embodiment, the peroxide oxidizer is selected among hydrogen peroxide, urea and hydrogen peroxide complex in a molar ratio 1:1, a perborate salt, a percarbonate salt.

In a further embodiment, the kit further comprises a peroxidase enzyme. Preferably, the peroxidase enzyme is selected among horseradish peroxidase, soybean peroxidase and sweet potato peroxidase. In a different embodiment, the peroxidase enzyme (or the conjugate thereof) can be added by the final user.

In an embodiment, the kit contains 8-amino-5-chloro-7-phenylpyrido[3,4-d]pyridazine-1,4(2H,3H)-dione in a first vial and the peroxide oxidizer in a second vial, and wherein the enhancer and the co-enhancer are present in the first vial or in the second vial or in both vials.

The kit reagents are present in the vials either in a liquid or solid state. If the kit reagents are in solid state, they can be present in powder or tablet form and have to be reconstituted in a liquid phase by addition of water or a buffering solution at the time of use.

The 8-amino-5-chloro-7-phenylpyrido[3,4-d]pyridazine-1,4(2H,3H)-dione and the peroxide oxidizer are best formulated in different vials, as to prolong their shelf life. Enhancers and co-enhancers, as well as other additives, such as chelators and stabilizers, can be added to either 8-amino-5- chloro-7-phenylpyrido[3,4-d]pyridazine-1,4(2H,3H)-dione or peroxide oxidizer vials, or both. The two vials also contain buffering substances that upon mixing generate a chemiluminescent substrate, or "Working Solution", having a pH value suitable for performing the assay.

The peroxidase enzyme or a conjugate thereof—if present in the kit—is not stored together with its substrate component (i.e. the peroxide oxidizer), but in a third vial.

The term "assay" means the detection, semi-quantification and quantification of an analyte. Typically, the implementation of an assay requires to relate the light output to the amount of peroxidase used. The emission of light is thus detected or measured so that the presence or the amount of analyte is related to the production of light.

According to the present disclosure, the implementation of an assay requires to relate the light output generated by the chemiluminescent reaction of a chemiluminescent compound reacted with a peroxidase enzyme, an enhancer, a co-enhancer and a peroxide oxidizer to the amount of any of the reaction partners (i.e. any one of (8-amino-5-chloro-7-phenylpyrido[3,4-d]pyridazine-1,4(2H,3H)-dione, the peroxidase enzyme, the peroxide oxidizer, the enhancer, and the co-enhancer). According to a preferred embodiment, the light output is related to the amount of the peroxidase enzyme used.

In performing the assay for detecting the analyte of interest (either in a qualitative or in a quantitative manner), the peroxidase enzyme is in the form of a conjugate with a detection reagent for the analyte to be detected. The detection reagent can be selected from an antibody, a nucleotide, an oligonucleotide or a nucleic acid molecule according to what kind of analyte is to be detected. The detection reagent conjugated to the peroxidase enzyme can be either a detection reagent able to specifically bind the analyte or a secondary detection reagent able to bind the detection reagent that specifically bind the analyte.

The chemiluminescent reactions of this invention are applicable to the detection and quantification of analytes, using, for example, the formation of a bond between the analyte (e.g. a protein or a nucleic acid molecule) and a solid support (e.g. a membrane or a microtiter plate) and using the peroxidase enzyme as tracer. The luminescent reaction is initiated by adding the chemiluminescent substrate as herein disclosed to the solid support (previously reacted with the analyte containing sample) and subsequently adding the peroxidase enzyme containing solution to the solid support. The emission of light is prolonged and can be measured by film, camera or other instrumentation.

Chemiluminescent assays based on the chemiluminescent substrate according to the present disclosure include dot blot and Western blot assays for proteins and Southern and Northern Blots assays for nucleic acids.

The blot assays based on the chemiluminescent substrate according to the present disclosure use gel electrophoresis to separate the analyte of interest (a protein or a nucleic acid molecule) from the other components (other proteins or other nucleic acid molecules) present in the sample to be tested. The analyte and the other components are then transferred to a membrane, where they are probed (detected) using the chemiluminescent substrate as disclosed herein and a detection reagent able to bind specifically the analyte of interest, wherein the detection reagent is conjugated to the peroxidase enzyme.

Figure 13:
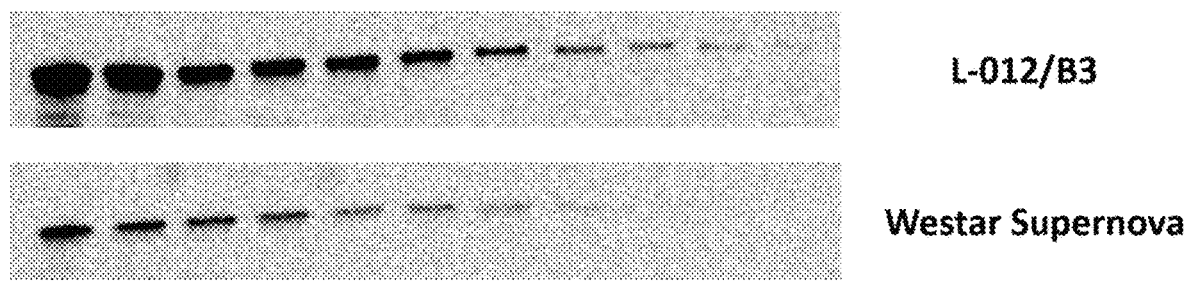
FIG. 13 shows Western Blots of Human IKBα obtained with L012/B3 substrate and a luminol based substrate, Westar Supernova.

A comparison between Western Blots obtained using an L-012 based substrate (B3/Example 10) of the present invention and a commercially available luminol based substrate (Westar Supernova by Cyanagen) is described in Example 12. As shown in FIG. 13, the L-012 based substrate of the present invention allows the detection of about three more bands with respect to the luminol based substrate.

Chemiluminescent assays based on the chemiluminescent substrate of this invention also include enzyme immunoassays (EIA), like for example ELISA assays. Enzyme immunoassays are especially useful for detecting analytes present in the sample in extremely small quantities, such as tumor markers, thyroid hormones, virus proteins (e.g. HIV, HCV, HPV proteins), or steroid hormones (e.g. estradiol, aldosterone). Performing an ELISA assay for detecting an analyte involves at least one detection reagent with specificity for the analyte of interest. The analyte within the sample is immobilized on a solid support (usually a polystyrene microtiter plate) either non-specifically (via adsorption to the solid support surface) or specifically (via capture by another detection reagent specific to the same analyte to the solid support surface, in a "sandwich ELISA"). After the analyte is immobilized onto the solid support surface, the detection reagent is added, forming a complex with the analyte. The detection reagent can be covalently linked to a peroxidase enzyme as tracer, or can itself be detected by a secondary detecting reagent that is linked to a peroxidase enzyme through (bio)conjugation (like for example via biotin or streptavidin). Between each step, the plate is typically washed with a mild detergent solution to remove any proteins or antibodies that are not specifically bound. After the final wash step, the plate is developed by adding the chemiluminescent substrate herein described and—in the case the detection reagent is not directly conjugated to the peroxidase enzyme—the solution containing the peroxidase enzyme conjugated to the secondary detection reagent to produce a light signal, which indicates the quantity of analyte in the sample.

Figure 14:
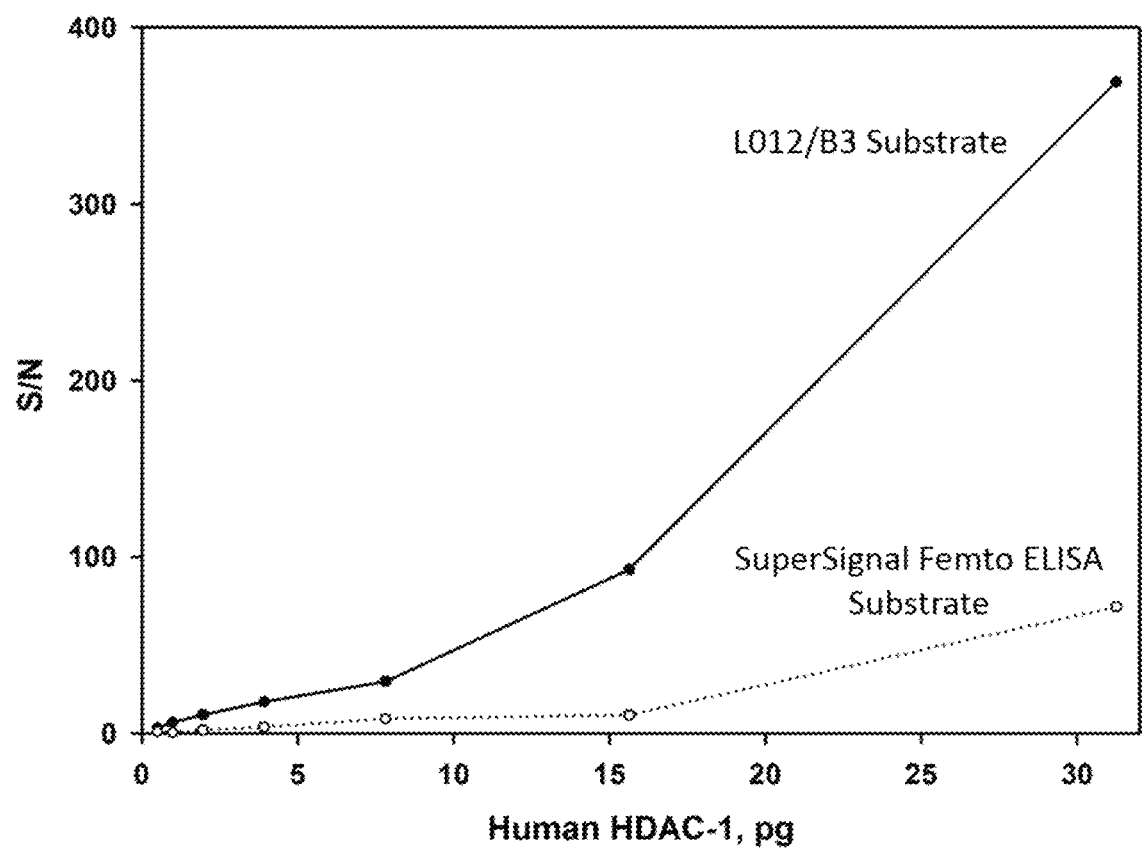
FIG. 14 shows an ELISA dose-response curve for Human HDAC-1 for L012/B3 substrate and a Luminol based Substrate, SuperSignal Femto ELISA.

Example 13 describes a Human HDAC-1 ELISA Assay, wherein the detection is carried out with L-012 based substrate (B3/Example 10) of the present invention and a commercially available luminol based substrate (SuperSignal Femto ELISA, by Thermo Scientific). As it can be observed in FIG. 14, the L-012/B3 substrate of this invention outperforms the luminol based substrate by a factor about five, in terms of sensitivity.

Figure 2:
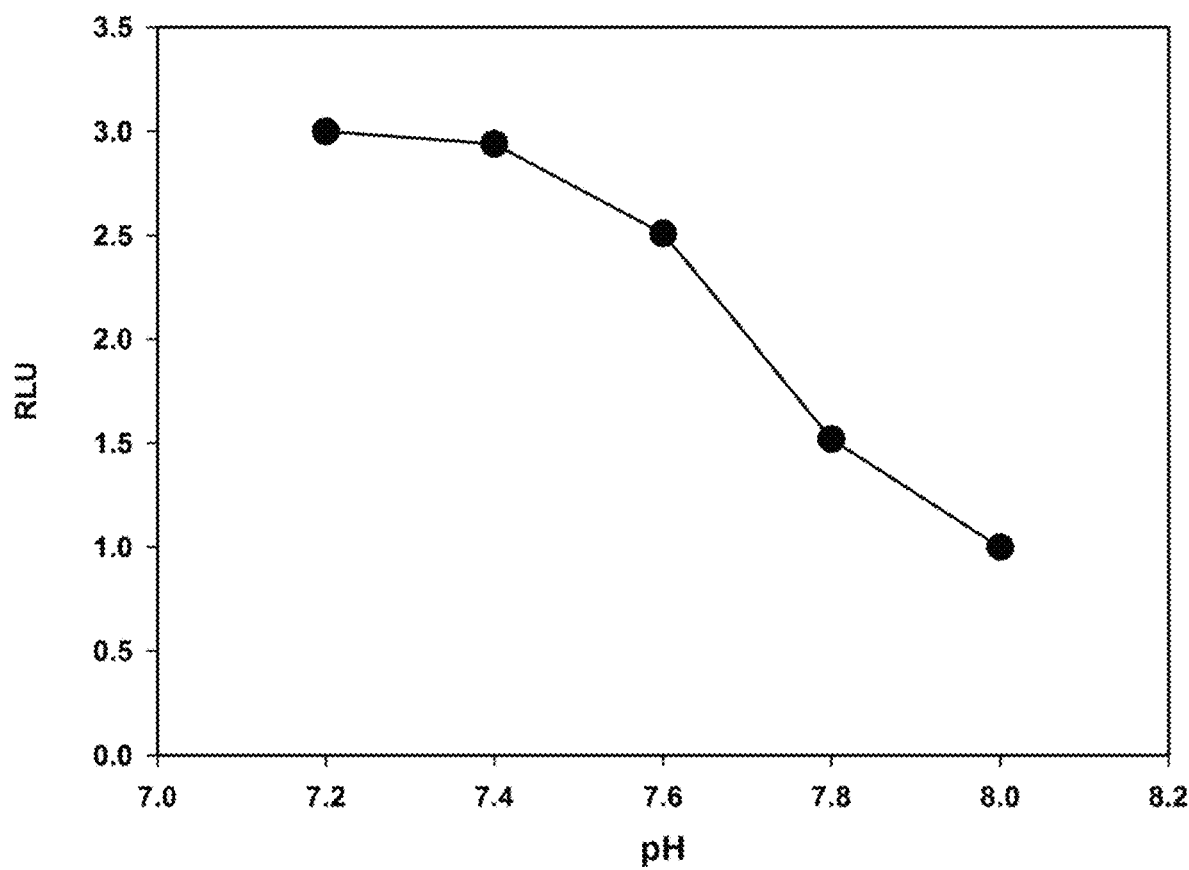
FIG. 2 shows a graph of the pH dependence of the chemiluminescent signal for the L-012/peroxide/SPTZ system.

L-012 chemiluminescent substrates enhanced with SPTZ according to the present invention produce a chemiluminescent signal about three times higher than an optimized Luminol/SPTZ substrate, as shown in Example 1, FIG. 2. Examples 3 to 11 illustrate the effect of adding co-enhancers to L-012 chemiluminescent substrates enhanced with anionic N-alkylphenothiazines in presence of a co-enhancer selected from 4-dialkylaminopyridines and N-azoles.

pH Dependence of the L-012/Peroxide/Peroxidase Chemiluminescent Reaction Enhanced by 3-(10'-phenothiazinyl)propane-1-sulfonate (SPTZ), (Example 1)

The pH optimum of HRP is in the range of 6.0 to 6.5; activity at 7.5 is 84% of the maximum. The enzyme is most stable in the pH range of 5.0 to 9.0. [Schomberg et al. Enzyme Handbook 7, EC 1.11.1.7:1-6 (1993)]. On the other hand, the non-enzymatic chemiluminescent oxidation of luminol by peroxide reaches its maximum efficiency at about pH 11.0 for millimolar peroxide concentration [Merenyi G. and Lind Johan S. "Role of a peroxide intermediate in the chemiluminescence of luminol. A mechanistic study." *Journal of the American Chemical Society* 102.18 (1980): 5830-5835]. The enhanced chemiluminescent oxidation of luminol catalyzed by peroxidase is most efficient at pH 8.4-8.6 for typical enhancers such as p-iodophenol [Thorpe et al. "Phenols as enhancers of the chemiluminescent horseradish peroxidase-luminol-hydrogen peroxide reaction: application in luminescence-monitored enzyme immunoassays." *Clinical chemistry* 31.8 (1985): 1335-1341], p-iodophenylboronic acid [Kricka, et al. "Synthesis and characterization of 4-iodophenylboronic acid: a new enhancer for the horseradish peroxidase-catalyzed chemiluminescent oxidation of luminol." *Analytical biochemistry* 240.1 (1996): 119-125] and, more recently, 3-(10'-phenothiazinyl)propane-1-sulfonate (SPTZ) [Marzocchi et al. "Chemiluminescent detection systems of horseradish peroxidase employing nucleophilic acylation catalysts." *Analytical biochemistry* 377.2 (2008): 189-194]. This pH optimum of 8.4-8.6 is a compromise between the turnover optimum of HRP (6.0-6.5) and the peroxide oxidation of luminol (pH 11.0).

In contrast to the luminol systems, the L-012/peroxide/peroxidase chemiluminescent reaction enhanced by 3-(10'-phenothiazinyl)propane-1-sulfonate (SPTZ) reaches its optimum at pH 7.2 or below, FIG. 2.

pH Dependence of the Chemiluminescent Signal in L-012/Peroxide/SPTZ Substrates in the Presence of Co-Enhancers (Example 7 and 8).

The addition of co-enhancers (MORP, Example 7; Imidazole, Example 8) to L-012/peroxide/SPTZ substrates has no influence on the pH optimum of the chemiluminescent signal, which is still centered around pH 7.0, (MORP, FIG. 9; imidazole, FIG. 10). Again, this is in stark contrast to the corresponding luminol/peroxide/SPTZ/co-enhancer substrates (MORP, pH optimum at pH 9.0 [ ]; imidazole, pH optimum: 8.6 [ ].

Dependence of the Chemiluminescent Signal on the Concentration of L-012 in L-012/Perborate/SPTZ/MORP Substrates (Example 3)

Another remarkable difference between Luminol and L-012 substrates is the much smaller amount of chemiluminescent material needed to reach optimum signal level. For example, in L-012/perborate/SPTZ/MORP substrates of Example 3 (Example 3), a concentration of L-012 of just around 0.15 mM is sufficient to reach a plateau level in signal output, FIG. 4. A similar behavior is observed in other formulations with L-012, such as L-012/perborate/SPTZ/imidazole substrates. On the other hand, optimized Luminol Substrates (Luminol/A1-A3 substrates Example 10) require a much higher concentration of luminol, 5.0 mM. Thus, L-012 substrates require 33 times less chemiluminescent material then Luminol based substrates.

Dependence of the Chemiluminescent Signal on the Concentration of SPTZ in L-012/Perborate/SPTZ/MORP Substrates (Example 4)

Figure 5:
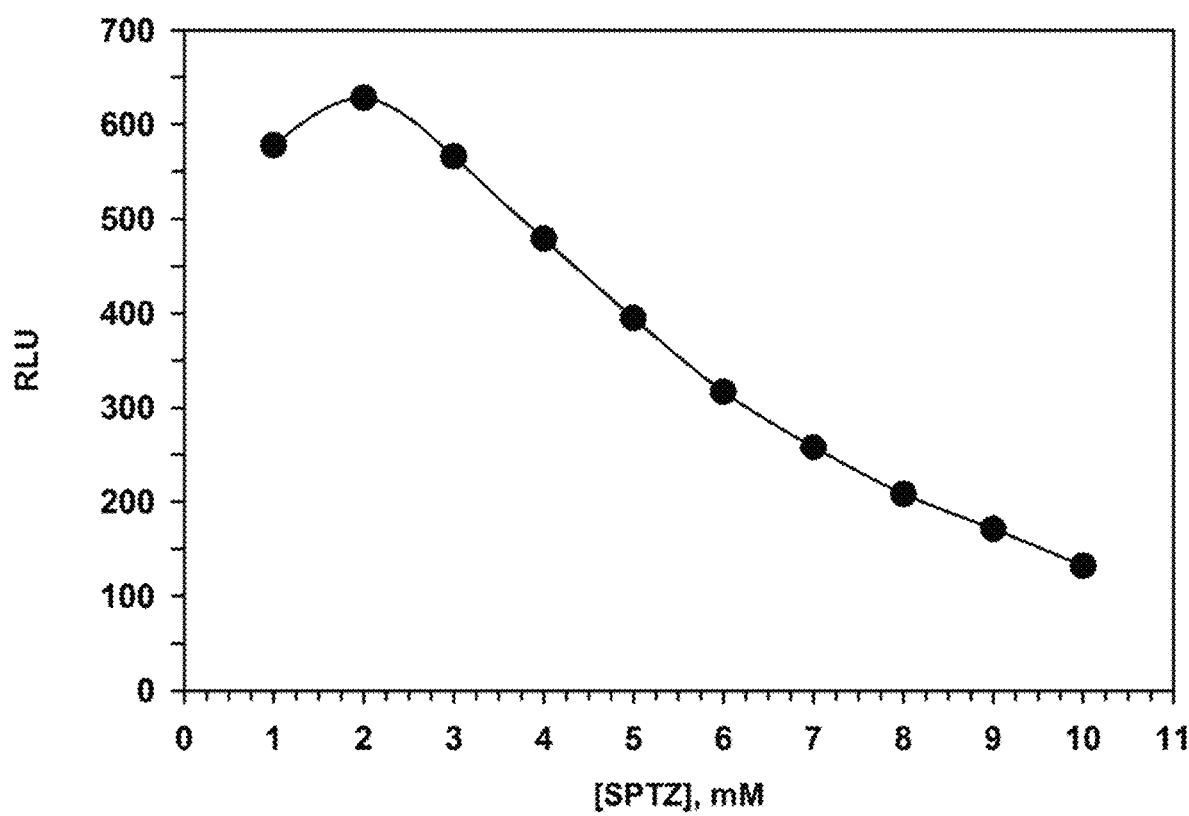
FIG. 5 shows the dependence of chemiluminescent signal on SPTZ concentration in the L-012/perborate/SPTZ/MORP substrate.

Signal level reaches a peak at values comprised between 2 and 3 mmol of SPTZ enhancer in L-012/perborate substrates where the co-enhancer is MORP, FIG. 5. Similar results were obtained with imidazole as co-enhancer.

Dependence of the Chemiluminescent Signal on the Concentration of Co-Enhancers in L-012/Perborate/SPTZ/Co-Enhancer (MORP; Imidazole) Substrates (Example 5, MORP; Example 9, Imidazole)

Co-enhancers such as MORP and imidazole have a very powerful effect on L-012/perborate substrates enhanced with SPTZ. Both co-enhancers increase light output by more than one order of magnitude 18 times (MORP, Figure to 6; imidazole, FIG. 10). While much less MORP is needed to reach a plateau in signal output compared to imidazole (3 mM vs. 50 mM), the effect of imidazole on light output is considerably stronger.

Dependence of the Chemiluminescent Signal on the Concentration of Perborate in L-012/Perborate/SPTZ/MORP Substrates (Example 6)

Figure 7:
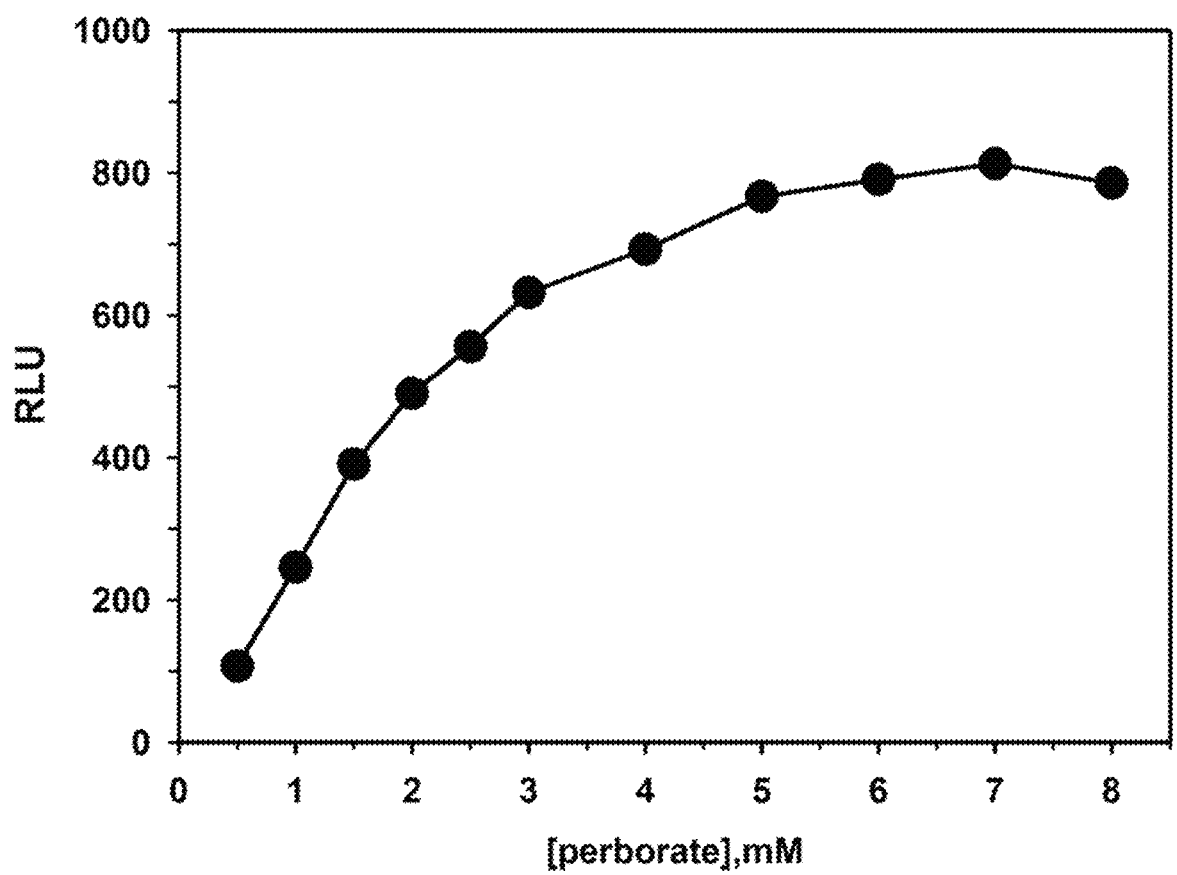
FIG. 7 shows the dependence of the chemiluminescent signal on perborate concentration in the L-012/perborate/SPTZ/MORP substrate.

In Example 6, FIG. 7, it is observed that the amount of perborate needed to achieve maximum signal in L-012/perborate/SPTZ/MORP substrates in about 6 mM. At perborate values higher than 7 mm, signal output starts to decrease. Similar results were recorded for the L-012/perborate/SPTZ/imidazole substrates.

Comparison Between L-012 and Luminol Chemiluminescent Peroxidase Substrates (Example 10)

Figure 11:
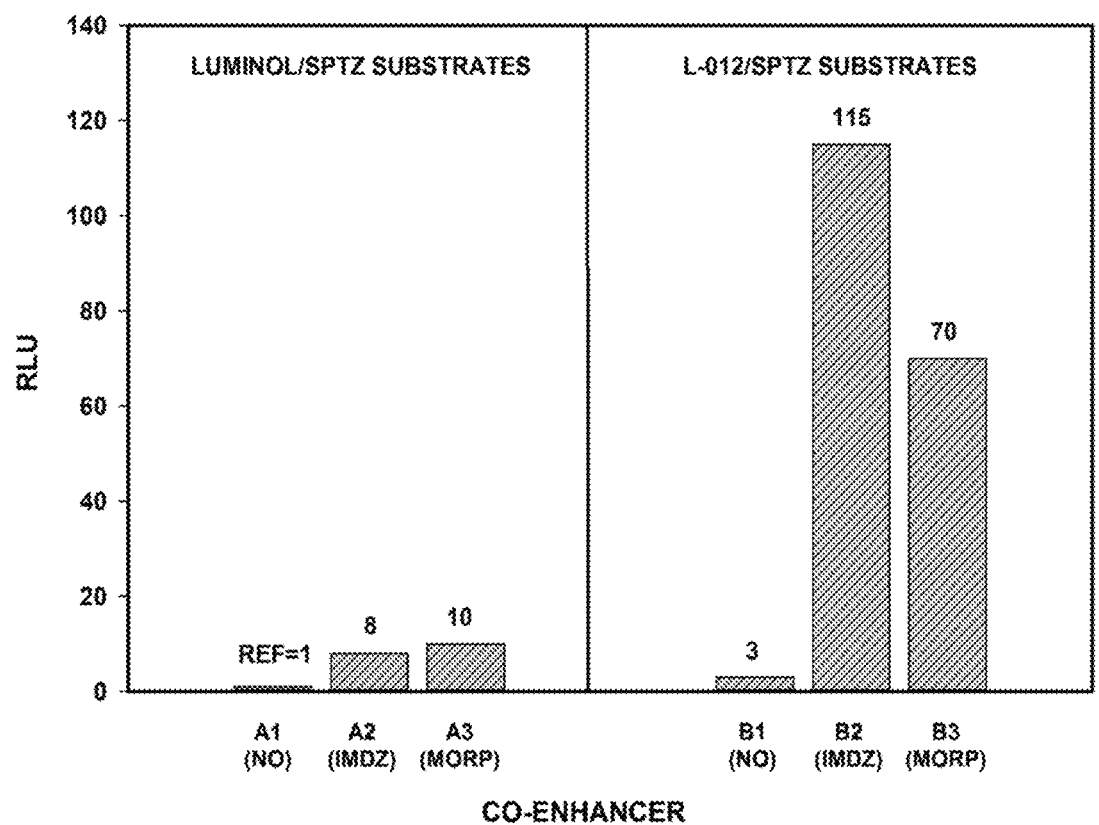
FIG. 11 shows a comparison between initial chemiluminescent signal in luminol/perborate/SPTZ and L-012/perborate/SPTZ substrates in the absence and in the presence of MORP and imidazole co-enhancers.

When chemiluminescent substrates based on L-012 of the present invention are compared to optimized luminol substrates several major differences emerge. In particular: (a) pH optimum for L-012 substrates is between 1.5 to 2 pH units lower than for luminol substrates; (b) effective concentration of L-012 is more than 30 times lower than that of luminol; (c) the effect of co-enhancers is much stronger in SPTZ enhanced L-012 substrates, compared to SPTZ enhanced substrates (FIG. 11); (d) chemiluminescent light output of the L-012 substrates of this invention are one order of magnitude more intense than the nest luminol substrates available.

Conclusions

Surprisingly, the effect of co-enhancers in L-012 chemiluminescent substrates is considerably higher than in luminol chemiluminescent substrates. The chemiluminescent signal of an optimized Luminol/SPTZ substrate increases eight times upon addition of imidazole as co-enhancer, while MORP produces a ten-fold increase in signal. In contrast, inclusion of these co-enhancers in L-012/SPTZ chemiluminescent substrates increases signal output by about 40 times (imidazole) and 23 times (MORP), as shown in Example 10, and FIG. 11.

As a result, L-012 chemiluminescent substrates according to the present disclosure achieve a signal level one order of magnitude (7-12×) higher than the most potent known luminol substrate.

The following examples serve to illustrate specific aspects of the invention. However, they are not intended to limit the invention.

EXAMPLES

All the reagents used within the present application were purchased from Sigma-Aldrich, TCI Europe and Panreac.

SPTZ and CPTZ enhancers were synthesized according to the common general knowledge of the man skilled in the art. SPTZ: Marzocchi E, Grilli S, Della Ciana L, Prodi L, Mirasoli M, and Roda A (2008) Anal biochem, 377:189-194; CPTZ: Han, F, Chi, L, Wu, W, Liang, X, Fu, M, and Zhao, J. Photochem. Photobiol. A: Chemistry 196.1 (200R):10-23.

Chemiluminescent measurements were performed with a microplate, multilabel spectrometer, Victor$^3$ (Perkin-Elmer) on luminescence mode (no emission filter). Black 96 wells microplates were used, (Optiplate-96F).

HRP test solution was prepared diluting 15 µL of horseradish peroxidase (HRP) stock solution (20 mg/L) to 50 mL with buffer (concentration: 6 ng/mL). 28 µL of HRP were added to each well (228 µL final in-well volume). Thus, the HRP final amount in each well is 168 pg.

Example 1—pH Dependence of the L-012/Peroxide/Peroxidase Chemiluminescent Reaction at Various Levels of Sodium 3-(phenothiazin-10-yl)propane-1-sulfonate (SPTZ) Enhancer A series of chemiluminescent substrates was prepared with the following composition:

[L-012]=0.15 mM
[sodium perborate]=4 mM
[SPTZ]=0.1 mM
in 50 mM Tris/30 mM phosphate buffer, pH 7.2-8.0.

As a reference substrate, the following solution was prepared:
[Luminol]=5 mM
[sodium perborate]=4 mM
[SPTZ]=1.5 mM
in 150 mM Tris Buffer, pH 9.0.

Initial signal levels are plotted vs. pH, FIG. 2 (signal of reference substrate set to 1).

Figure 3:
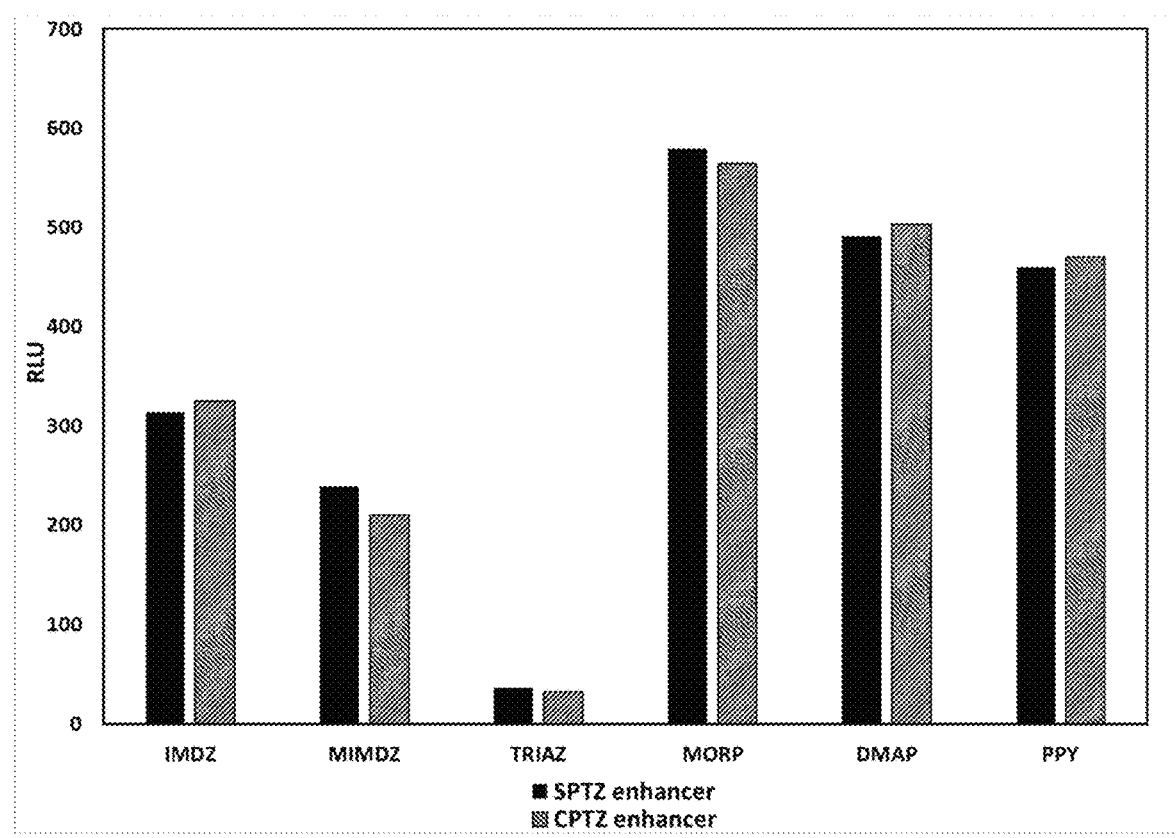
FIG. 3 shows a bar graph of the initial chemiluminescent signal of L-012/perborate substrates enhanced by SPTZ and CPTZ in the presence of co-enhancers imidazole (IMDZ); 1-methylimidazole (MIMDZ), 1,2,3-triazole (TRIAZ), 4-morpholinopyridine (MORP), 4-dimethylaminopyridine (DMAP), and 4-pyrrolidinopyridine (PPY).

Example 2—Screening of Co-Enhancers for the L-012/Peroxide/Peroxidase Chemiluminescent Reaction A chemiluminescent substrate was prepared with the following composition:
[L-012]=0.15 mM
[sodium perborate]=4 mM
[SPTZ]=1 mM; [CPTZ]=1 mM (enhancers)
in 50 mM Tris/30 mM phosphate buffer, pH 7.9
[co-enhancer]=1 mM Initial signal levels for each co-enhancer, imidazole, 1-methylimidazole, 1,2,3-triazole, 4-morpholinopyridine (MORP), 4-dimethylaminopyridine (DMAP), 4-pyrrolidinopyridine (PPY), are plotted as a bar graph, as shown in FIG. 3.

Example 3—Dependence of the Chemiluminescent Signal on the Concentration of L-012 in L-012/Perborate/SPTZ/MORP Substrates A series of chemiluminescent substrates was prepared with the following composition:
[L-012]=0.15 mM
[sodium perborate]=4 mM
[SPTZ]=3 mM (enhancer)
[MORP]=3 mM (co-enhancer)
in 50 mM Tris/30 mM phosphate buffer, pH 7.9.

Figure 4:
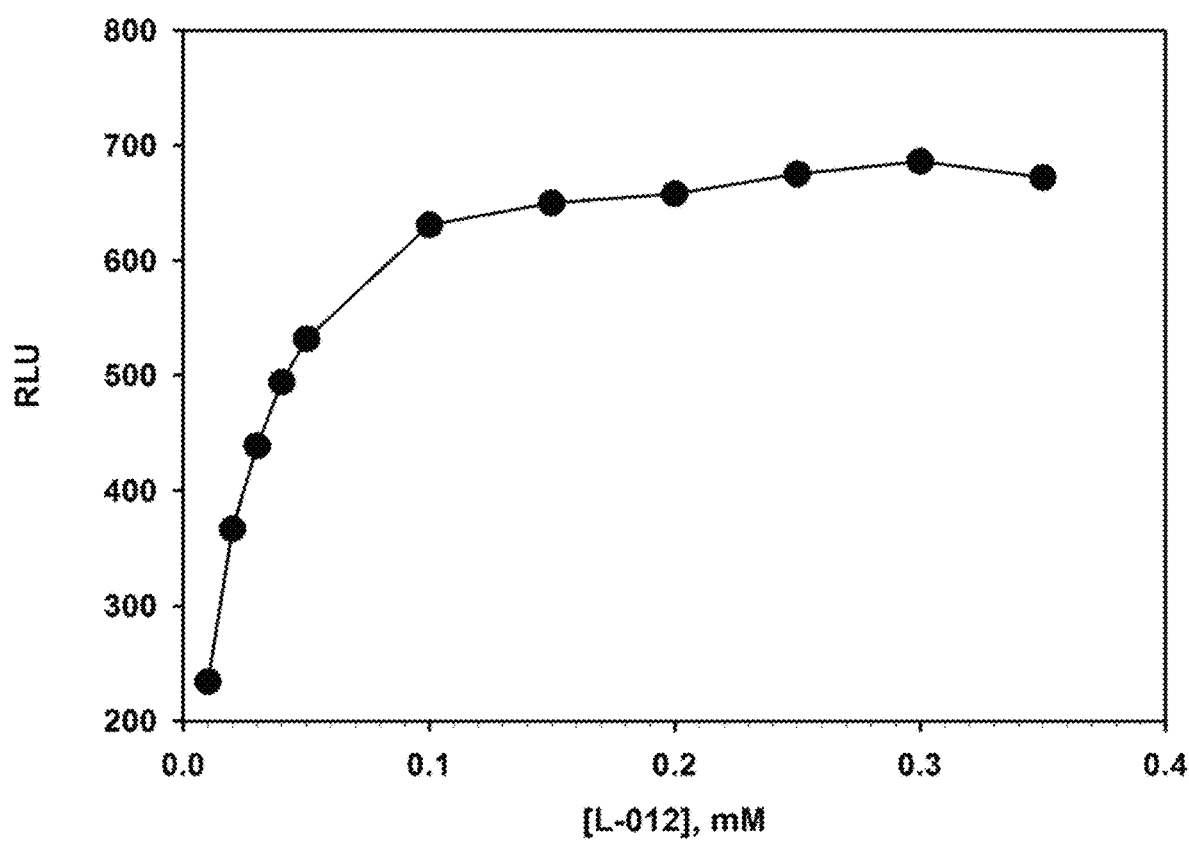
FIG. 4 shows the dependence of the chemiluminescent signal on L-012 concentration in the L-012/perborate/SPTZ/MORP substrate.

Initial signal levels are plotted vs. concentration of L-012, as shown in FIG. 4.

Example 4—Dependence of the Chemiluminescent Signal on the Concentration of SPTZ in L-012/Perborate/SPTZ/MORP Substrates A series of chemiluminescent substrates was prepared with the following composition:
[L-012]=0.15 mM
[sodium perborate]=4 mM
[SPTZ]=1-10 mM (enhancer)
[MORP]=3 mM (co-enhancer)
in 50 mM Tris/30 mM phosphate buffer, pH 7.9.

Initial signal levels are plotted vs. concentration of SPTZ, as shown in FIG. 5.

Example 5—Dependence of the Chemiluminescent Signal on the Concentration of MORP in L-012/Perborate/SPTZ/MORP Substrates A series of chemiluminescent substrates was prepared with the following composition:
[L-012]=0.15 mM
[sodium perborate]=4 mM
[SPTZ]=3 mM (enhancer)
[MORP]=0-6 mM (co-enhancer)
in 50 mM Tris/30 mM phosphate buffer, pH 7.9.

Figure 6:
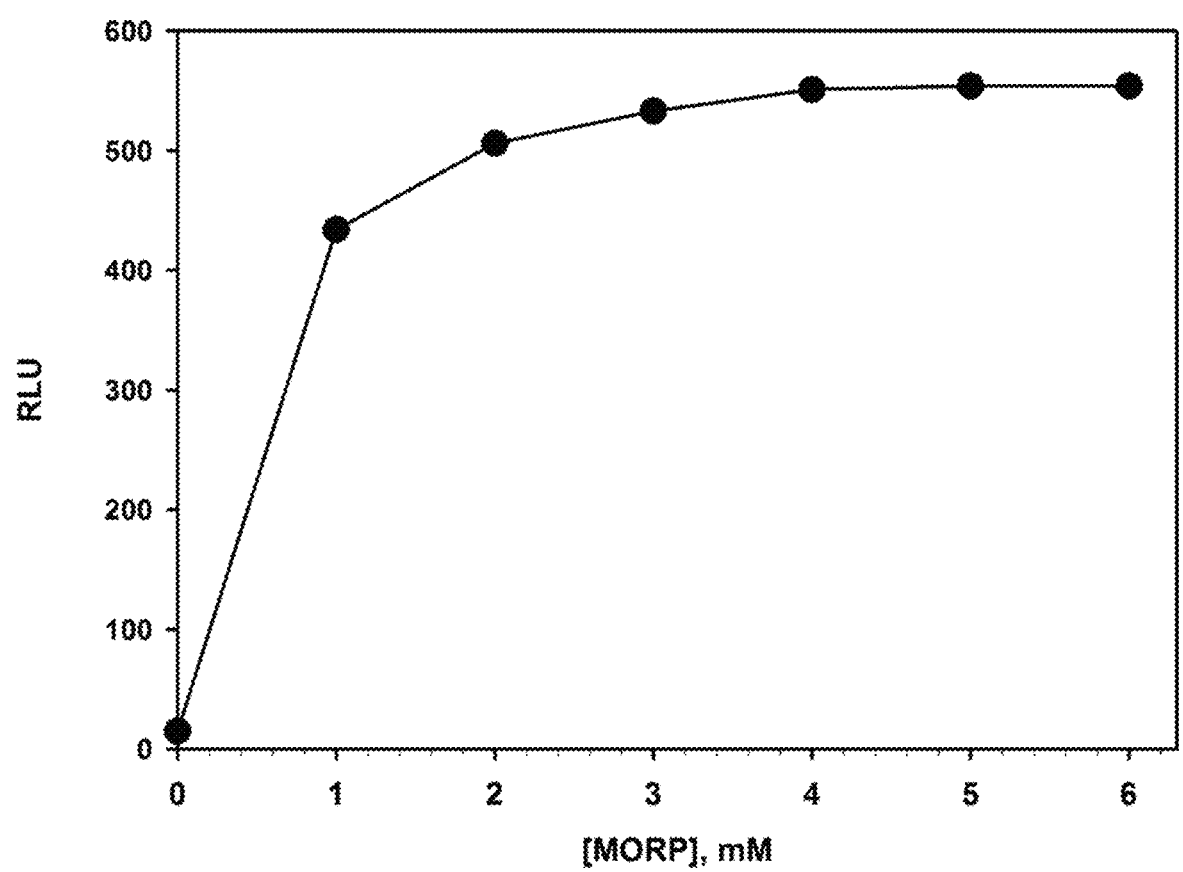
FIG. 6 shows the dependence of the chemiluminescent signal on MORP concentration in the L-012/perborate/SPTZ/MORP substrate.

Initial signal levels are plotted vs. concentration of MORP, as shown in FIG. 6.

Example 6—Dependence of the Chemiluminescent Signal on the Concentration of Perborate in L-012/Perborate/SPTZ/MORP Substrates A series of chemiluminescent substrates was prepared with the following composition:
[L-012]=0.15 mM
[sodium perborate]=0.5-8.0 mM
[SPTZ]=3 mM (enhancer)
[MORP]=3 mM (co-enhancer)
in 50 mM Tris/30 mM phosphate buffer, pH 7.9.

Initial signal levels are plotted vs. concentration of perborate, as shown in FIG. 7.

Example 7—pH Dependence of the Chemiluminescent Signal in L-012/Perborate/SPTZ/MORP Substrates A series of chemiluminescent substrates was prepared with the following composition:
[L-012]=0.15 mM
[sodium perborate]=4 mM
[SPTZ]=3 mM (enhancer)
[MORP]=3 mM (co-enhancer)
pH 5-9 (Tris buffer)

Figure 8:
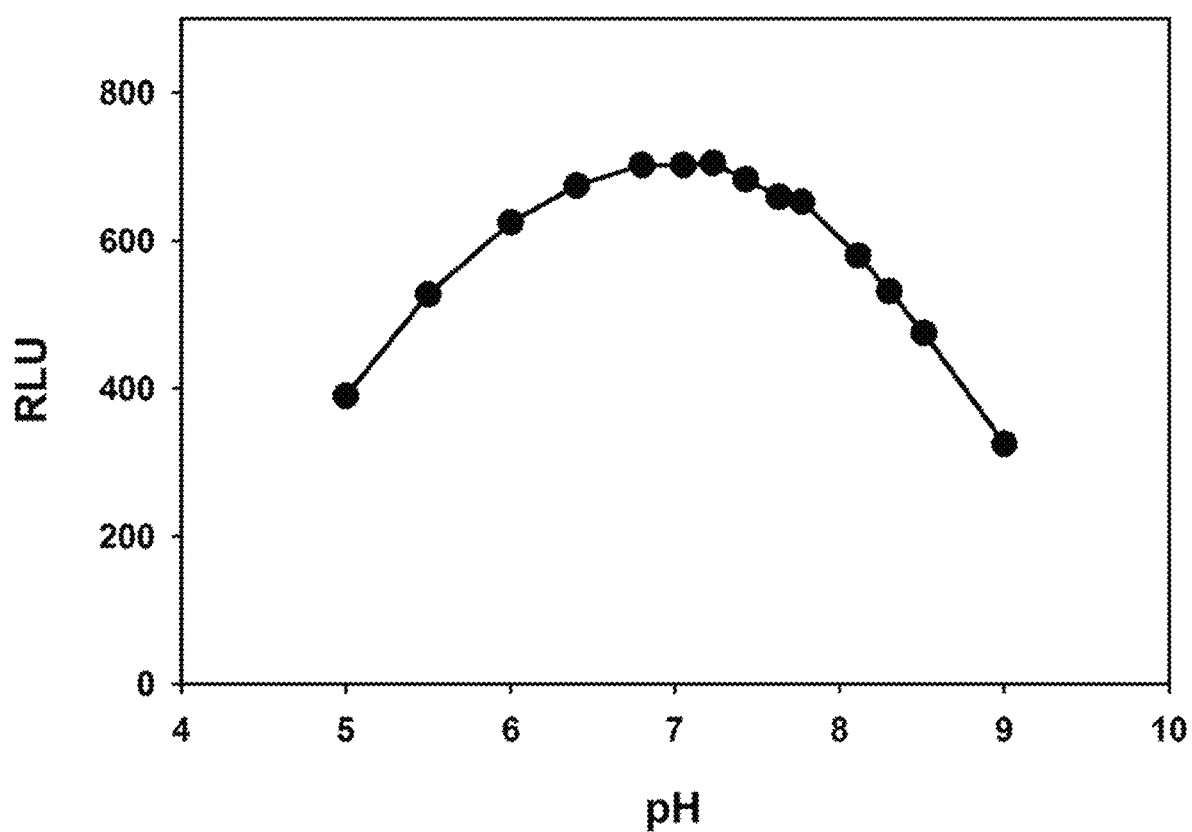
FIG. 8 shows the pH dependence of the chemiluminescent signal in the L-012/perborate/SPTZ/MORP substrate.

Initial signal levels are plotted vs. the concentration of perborate, as shown in FIG. 8.

Example 8—pH Dependence of the Chemiluminescent Signal in L-012/Perborate/SPTZ/Imidazole (IMDZ) Substrates A series of chemiluminescent substrates was prepared with the following composition:
[L-012]=0.15 mM
[sodium perborate]=4 mM
[SPTZ]=3 mM (enhancer)
[IMDZ]=50 mM (co-enhancer)
pH range 6.3-8.1

Figure 9:
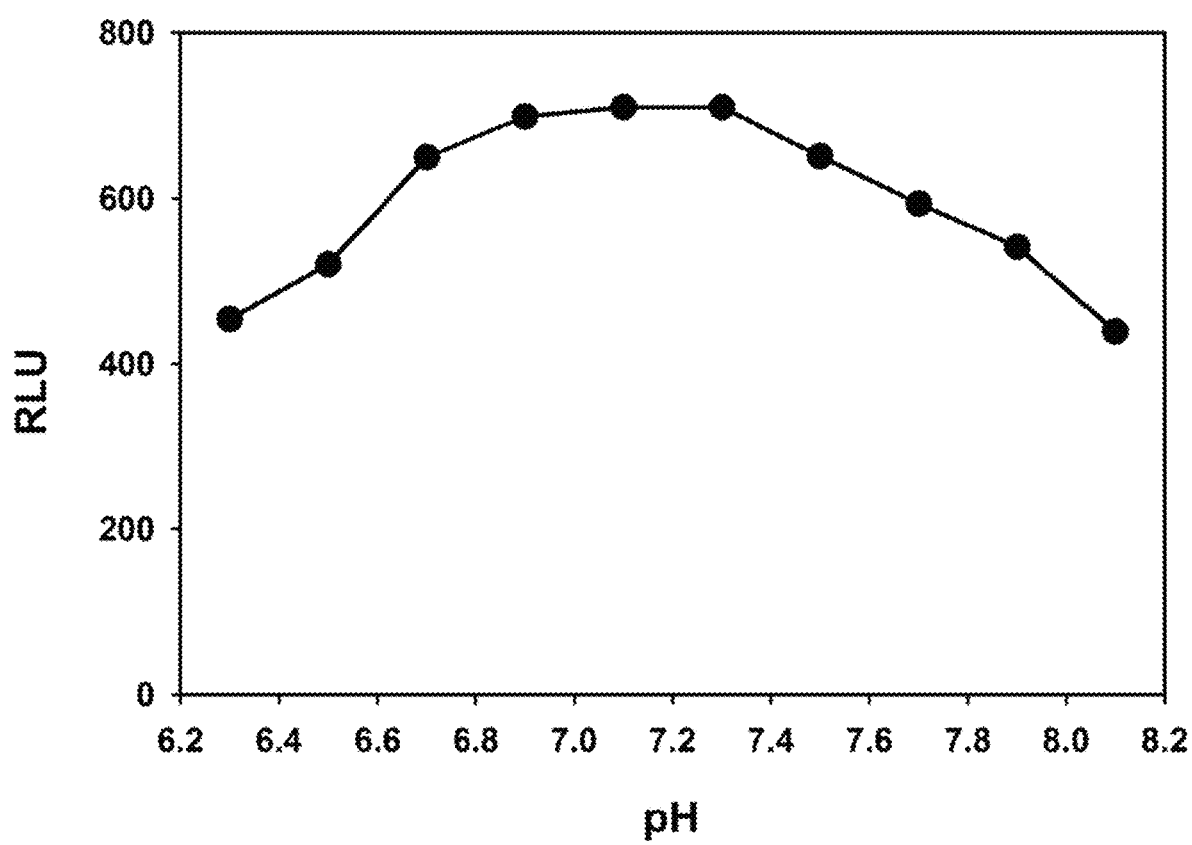
FIG. 9 shows the pH dependence of chemiluminescent signal in the L-012/perborate/SPTZ/imidazole substrate.

Initial signal levels are plotted vs. pH, as shown in FIG. 9.

Example 9—Dependence of the Chemiluminescent Signal on the Concentration of Imidazole (IMDZ) in L-012/Perborate/SPTZ/IMDZ Substrates A series of chemiluminescent substrates was prepared with the following composition:
[L-012]=0.15 mM
[sodium perborate]=4 mM
[SPTZ]=3 mM (enhancer)
[IMDZ]=0-100 mM (co-enhancer)
in 50 mM Tris Buffer, pH 7.1

Figure 10:
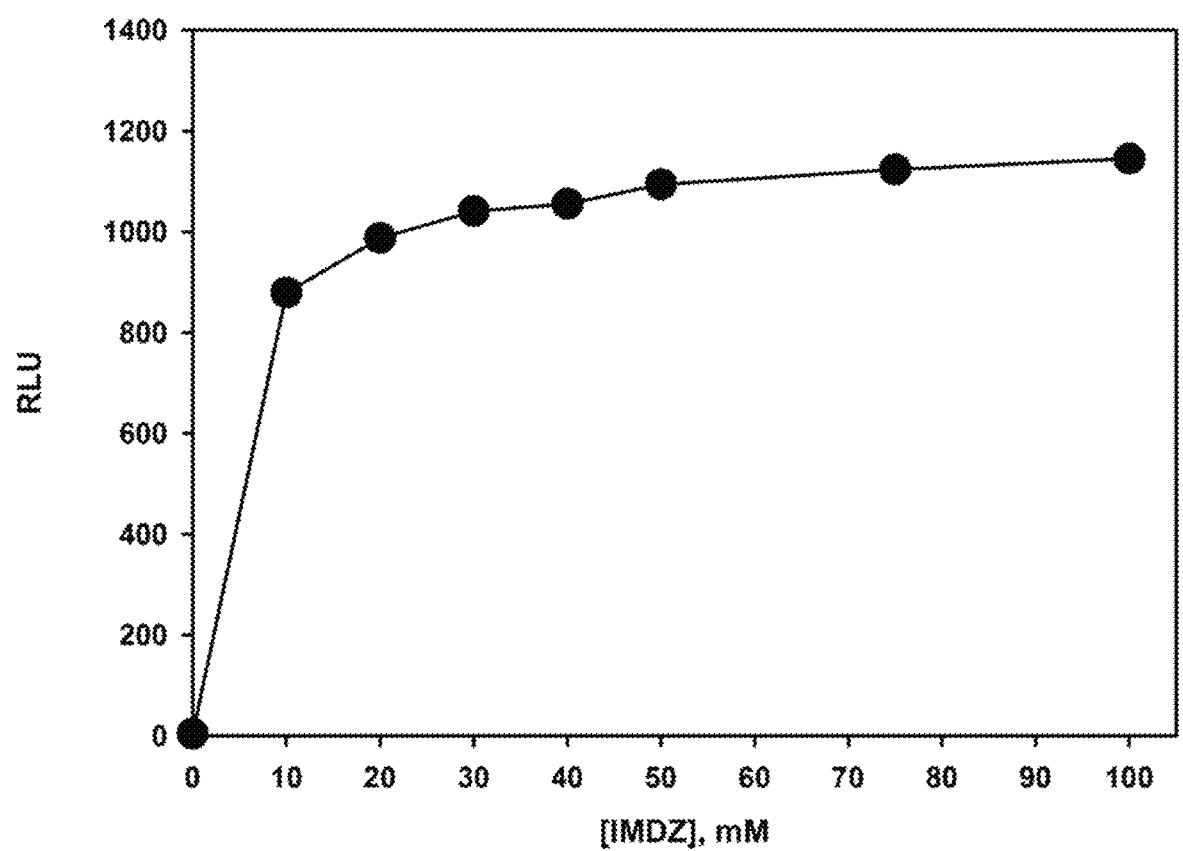
FIG. 10 shows the dependence of the chemiluminescent signal on imidazole concentration in the L-012/perborate/SPTZ/MORP substrate.

Initial signal levels are plotted vs. concentration of Imidazole (IMDZ), as shown in FIG. 10.

Example 10—Comparison Between Luminol and L-012 Chemiluminescent Substrates for Peroxidase The following chemiluminescent substrates were prepared:

Luminol Substrates
Luminol/A1 (NO: without co-enhancer; signal set to 1)
[Luminol]=5 mM
[perborate]=4 mM
[SPTZ]=3 mM
Tris Buffer 150 mM, pH 9.0
Luminol/A2 (IMDZ: imidazole as co-enhancer)
[Luminol]=5 mM
[perborate]=4 mM
[SPTZ]=3 mM
[IMDZ]=35 mM
Tris Buffer 150 mM, pH 9.0
Luminol/A3 (MORP: 4-morpholinopyridine as co-enhancer)
[Luminol]=5 mM
[perborate]=4 mM
[SPTZ]=3 mM
[MORP]=3 mM
Tris Buffer 150 mM, pH 9.0
L-012 Substrates
L012/B1 (NO: without co-enhancer)
[L-012]=0.15 mM
[perborate]=4 mM
[SPTZ]=3 mM
Tris-Phosphate Buffer 50/30 mM, pH 7.1
L012/B2 (IMDZ: Imidazole as co-enhancer)
[L-012]=0.15 mM
[perborate]=7 mM
[SPTZ]=2 mM
[IMDZ]=100 mM
Tris Buffer 50 mM, pH 7.1
L012/B3 (MORP: 4-morpholinopyridine as co-enhancer)
[L-012]=0.15 mM
[perborate]=4 mM
[SPTZ]=3 mM
[MORP]=3 mM
50 mM Tris/30 mM phosphate buffer, pH 7.9.

Initial chemiluminescent signal levels were recorded for each substrate. The signal produced by the luminol perborate/SPTZ without co-enhancer was taken as reference signal (REF), with its value set to unity.

Luminol substrates: NO (A1)=REF set to 1; IMDZ (A2) =8; MORP (A3)=10

L-012 substrates: NO (B1)=3; IMDZ (B2)=115; MORP (B3)=70

Results were plotted as a bar graph, as shown in FIG. 11.

Example 11—Chemiluminescent Signal Vs IMP Concentration for Chemiluminescent Substrate L-012/133 and Chemiluminescent Substrate Luminol/A3

Figure 12:
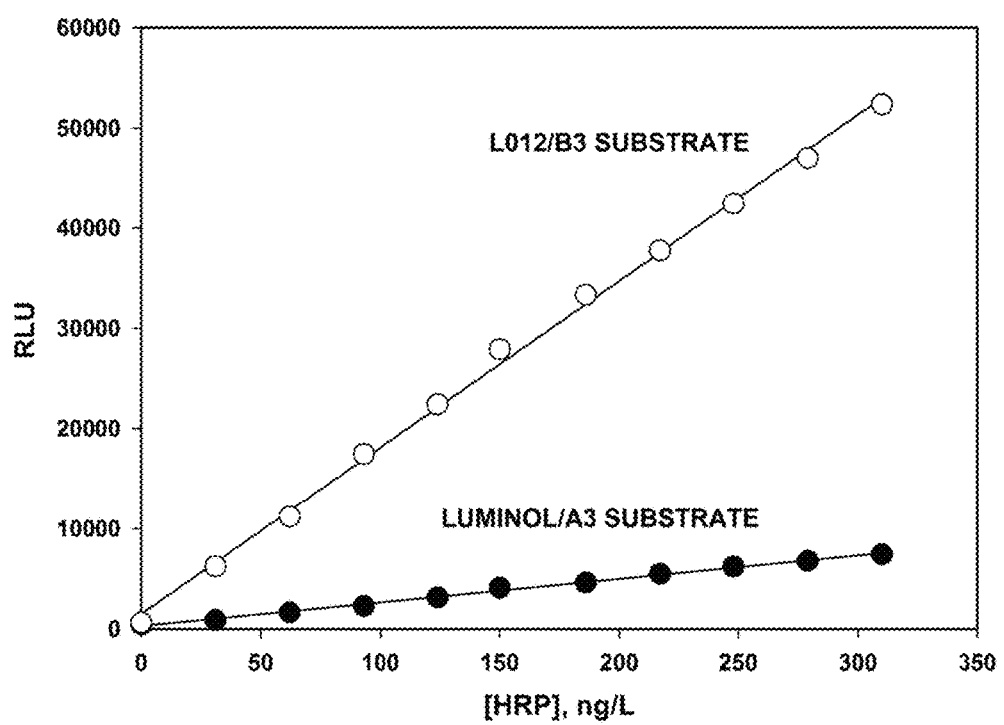
FIG. 12 shows a graph of the chemiluminescent signal as a function of the amount of horseradish peroxidase (HRP) for L012/B3 and Luminol/A3 substrates.

Chemiluminescent substrates L-012/B3 and Luminol/A3 were prepared as described in Example 11. 200 µL of these substrates of were dispensed in each well of a 96-wells plate. Horseradish peroxidase (HRP) (20 µg/mL) was diluted to obtain a 1600 ng/mL solution, from which various aliquots were dispensed into each well with the automated pump system of a Victor$^3$ (Perkin-Elmer) multilabel reader so as to achieve a series of dilutions spanning the 30-300 ng/L range. Column 1 in the plate was used as blank (just substrate, without adding the enzyme). Initial signals for the two substrates were plotted vs. HRP concentration, as shown in FIG. 12. Regression lines were calculated for each substrate. The regression slope of the L-012/B3 substrate is about seven times higher than for the Luminol/A3 substrate, while the measured background signal is similar for both substrates.

Example 12—Human IKBα Western Blot Assay

Purified human IKBα (nuclear factor of kappa light polypeptide gene enhancer in B-cells inhibitor, alpha; Abcam) was diluted to 1.5 ng/mL in electrophoresis reducing sample buffer and 1.5-fold dilutions were made. 5 µL of each dilution were separated by SDS-PAGE and the proteins transferred with Trans-Blot® Turbo™ Transfer System BIO-RAD. Membranes were blocked with 2% Amersham™ ECL™ Blocking Agent (GE Healthcare) in 1×PBS TWEEN®20 Buffer, then incubated with Rabbit anti-IKBα (Abcam) at 1:1000, followed by incubation with Anti-Rabbit IgG HRP (Abcam) at 1:500000. Chemiluminescent substrate L012/B3 (Example 11) and Westar Supernova (Cyanagen), a luminol based substrate, were used for detection with ImageQuant™ LAS 4000 (GE Healthcare) according to the manufacturer's instructions. Results are shown in FIG. 13.

Example 13—Human HDAC-1 ELISA Assay

Rabbit anti Human HDAC-1 (Abcam) was diluted in 50 mM carbonate/bicarbonate buffer pH 9.6 and two-fold dilutions were prepared starting from 20 ng/mL to 19.9 pg/mL. A 96 black microplate with clear flat bottom polystyrene (Corning) was coated with 50 µl/well at 4° C. overnight. Coating solution was removed and the plate was washed 6 times with 200 µl/well of PBS-Tween 0.01%. 100 µl of 3% ECL Blocking agent (GE Healthcare) in PBS-Tween 0.01% were added to each well and plate was incubated for 1 hour at room temperature. Blocking buffer was removed with a brief washing in PBS-Tween 0,01% and 100 µl of Goat Anti Rabbit-HRP (Abcam), diluted at the concentration 0.4 µg/mL, was added to each well for 30 minutes at room temperature. Goat Anti Rabbit-HRP solution was removed and the plate was washed 6 times with 200 µl/well of PBS-Tween 0.01%. 200 µl of chemiluminescent substrates (L012/B3, Example 11; SuperSignal ELISA Femto, a luminol-based substrate by Thermo Scientific) were added to each well and the plate was analyzed with Perkin Elmer Victor$^3$ analyzer at 60 and 120 seconds. A graph of Signal-to-Noise (S/N) vs. Human HDAC-1 (pg) is shown FIG. 14.

Naturally, while the principle of the invention remains the same, the details of construction and the embodiments may vary widely with respect to what has been described and illustrated by way of example, without departing from the scope of the present invention as defined in the appended claims.

The invention claimed is:

1. A method of producing enhanced light emission from 8-amino-5-chloro-7-phenylpyrido[3,4-d]pyridazine-1,4(2H, 3H)-dione (L-012) substrate by a chemiluminescent reaction with a horseradish peroxidase (HRP) enzyme or a conjugate thereof, an enhancer, a co-enhancer and a peroxide oxidizer, wherein the enhancer is 3-(10H-phenothiazin-10-yl)propane-1-sulfonic acid (SPTZ) or 4-(10H-phenothiazin-10yl) butane-1-sulfonic acid (SBTZ), the method comprises the following steps:
i. preparing a chemiluminescent substrate by mixing together in a Tris buffered solution, the 8-amino-5-chloro-7-phenylpyrido[3,4-d]pyridazine-1,4(2H,3H)-dione, the enhancer SPTZ or SBTZ, the co-enhancer and the peroxide oxidizer, and ii. adding the HRP enzyme or a conjugate thereof to the prepared chemiluminescent substrate;
wherein the co-enhancer is selected from the group consisting of imidazole, 1-methylimidazole, 4-morpholinopyridine (MORP), 4-dimethylaminopyridine (DMAP) and 4-pyrrolidinopyridine (PPY); and
wherein the pH of the chemiluminescent substrate prepared in step i. is in the range of 7.0 to 7.2.

2. The method according to claim 1, wherein the peroxide oxidizer is selected from the group consisting of hydrogen peroxide, urea and hydrogen peroxide complex in a molar ratio 1:1, a perborate salt, a percarbonate salt.

3. The method according to claim 1, wherein the concentration of the chemiluminescent compound, 8-amino-5-chloro-7-phenylpyrido[3,4-d]pyridazine-1,4(2H,3H)-dione, in the chemiluminescent substrate is between 0.01 mM and 1 mM.

4. The method according to claim 1, wherein the concentration of the enhancer SPTZ or SBTZ in the chemiluminescent substrate is comprised between 0.1 mN and 10 mM.

5. The method according to claim 1, wherein the concentration of the co-enhancer in the chemiluminescent substrate is between 0.1 mM and 100 mM.

6. The method according to claim 1, wherein the concentration of the peroxide in the chemiluminescent substrate is between 0.1 mM and 10 mM.

7. The method according to claim 1, wherein the chemiluminescent substrate. contains:
   a. 8-amino-5-chloro-7-phenylpyrido[3,4-d]pyridazine-1,4(2H,3H)-dione at a concentration between 0.01 mM and L mM;
   b. the enhancer SPTZ or SBTZ at a concentration between 0.1 and 10 mM;
   c. the co-enhancer at a concentration between 0.1 mM and 100 mM; and
   d. the peroxide oxidizer at a concentration between 0.1 mM and 10 mM.

8. The method of claim 1, wherein the enhancer is 3-(10H-phenothiazin-10-yl)propane-1-sulfonic acid or its salts, and the co-enhancer is imidazole, or 4-morpholinopyridine (MORP).

* * * * *